United States Patent [19]

Shih et al.

[11] Patent Number: 4,882,333

[45] Date of Patent: Nov. 21, 1989

[54] N-(5,6,7,8-TETRAHYDROPYRIDO[2,3-D]PYRIMIDIN-6-YL-ALKANOYL)-GLUTAMIC ACID DERIVATIVES

[75] Inventors: Chuan Shih, Indianapolis, Ind.; Edward C. Taylor, Princeton, N.J.

[73] Assignees: The Trustees of Princeton University, Princeton, N.J.; Eli Lilly and Company, Indianapolis, Ind.

[21] Appl. No.: 198,201

[22] Filed: May 25, 1988

[51] Int. Cl.$^4$ .................. A61K 31/505; C07D 475/08
[52] U.S. Cl. ...................................... 514/258; 544/279
[58] Field of Search ........................ 544/279; 514/258

[56] References Cited
U.S. PATENT DOCUMENTS 4,684,653 8/1987 Taylor et al. .................. 544/279

Primary Examiner—Mukund J. Shah
Assistant Examiner—Carol L. Cseh
Attorney, Agent, or Firm—Mathews, Woodbridge, Goebel, Pugh & Collins

[57] ABSTRACT

N-alkanoylglutamic acid derivatives in which the alkanoyl group is substituted with the 2-amino-4-hydroxy-5,6,7,8-tetrahydropyrido[2,3-d]pyrimidine-6-yl or 2,4-diamino-5,6,7,8-tetrahydropyrido[2,3-d]pyrimidin-6-yl group are antineoplastic agents. Typical embodiments are N-[6-(2-amino-4-hydroxy-5,6,7,8-tetrahydropyrido[2,3-d]pyrimidin-6-yl)hexanoyl]-L-glutamic acid and N-[4-{-(2-amino-4-hydroxy-5,6,7,8-tetrahydropyrido[2,3-d]pyrimidin-6-yl ethyl}cyclohex-1-yl]-L-glutamic acid.

13 Claims, No Drawings

N-(5,6,7,8-TETRAHYDROPYRIDO[2,3-D]PYRIMIDIN-6-YL-ALKANOYL)-GLUTAMIC ACID DERIVATIVES

The present invention pertains to the individual diastereomers and to the diastereomeric mixture of glutamic acid derivatives of the formula:

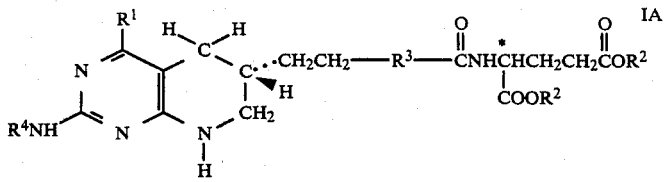

or

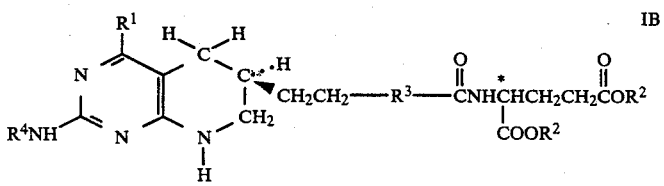

in which:
 $R^1$ is —OH or —NH$_2$;
 $R^2$ hydrogen or a carboxy protecting group;
 $R^3$ is a carbon-carbon bond, alkylene of 1 to 4 carbon atoms, or cyclohexylene;
 $R^4$ is hydrogen or an amino protecting group; and the configuration about the carbon atom designated * is S.

The compounds of Formula IA and IB have an inhibitory effect on one or more enzymes which utilize folic acid, and in particular metabolic derivatives of folic acid, as a substrate. The compounds thus can be used, alone or in combination, to inhibit the growth of those neoplasms which otherwise depend upon the enzymes so inhibited.

The invention also pertains to the pharmaceutically acceptable salts of the compounds of Formula IA and IB, to processes for the preparation of these compounds and their salts, to a method of combatting neoplastic growth in a mammal, and to pharmaceutical compositions containing these compounds or their salts.

The term alkylene as used herein denotes a straight or branched divalent aliphatic group of from 1 to 4 carbon atoms including methylene, ethylene, trimethylene, tetramethylene, 1,1-propylidene, 2,2-propylidene, 1,2-propanediyl, 2,3-butanediyl, etc. Analogously, cyclohexylene denotes a divalent cycloalkane group of 6 carbon atoms including 1,2-cyclohexylene, 1,3-cyclohexylene, and 1,4-cyclohexylene.

The protecting groups designated by $R^2$ and $R^4$ and utilized herein denote groups which generally are not found in the final therapeutic compounds but which are intentionally introduced during a portion of the synthesis to protect a group which otherwise might react in the course of chemical manipulations, thereafter being removed at a later stage of the synthesis. Since compounds bearing such protecting groups thus are of importance primarily as chemical intermediates (although some derivatives also exhibit biological activity), their precise structure is not critical. Numerous reactions for the formation and removal of such protecting groups are described in a number of standard works including, for example, "Protective Groups in Organic Chemistry", Plenum Press, London and New York, 1973; Greene, Th. W. "Protective Groups in Organic Synthesis", Wiley, New York, 1981; "The Peptides", Vol. I, Schröder and Lubke, Academic Press, London and New York, 1965; "Methoden der organischen Chemie", Houben-Weyl, 4th Edition, Vol.15/I, Georg Thieme Verlag, Stuttgart 1974.

A carboxy group can be protected as an ester group which is selectively removable under sufficiently mild conditions not to disrupt the desired structure of the molecule, especially a lower alkyl ester such as methyl or ethyl and particularly one which is branched at the 1-position such as t.-butyl; and such lower alkyl ester substituted in the 1- or 2-position with (i) lower alkoxy, such as for example, methoxymethyl, 1-methoxyethyl, and ethoxymethyl, (ii) lower alkylthio, such as for example methylthiomethyl and 1-ethylthioethyl; (iii) halogen, such as 2,2,2-trichloroethyl, 2-bromoethyl, and 2-iodoethoxycarbonyl; (iv) one or two phenyl groups each of which can be unsubstituted or mono-, dior trisubstituted with, for example lower alkyl such as tert.-butyl, lower alkoxy such as methoxy, hydroxy, halo such as chloro, and nitro, such as for example, benzyl, 4-nitrobenzyl, diphenylmethyl, di-(4-methoxyphenyl)-methyl; or (v) aroyl, such as phenacyl. A carboxy group can also be protected in the form of an organic silyl group such as tri-lower alkylsilyl, as for example trimethylsilyloxycarbonyl.

Amino groups similarly can be protected as an amide utilizing an acyl group which is selectively removable under mild conditions, especially formyl, a lower alkanoyl group which is branched at the 1-position, particularly tertiary alkanoyl such as pivaloyl, or a lower alkanoyl group which is substituted in the 1-position, as for example trifluoroacetyl.

Preferred compounds are those wherein $R^1$ is —OH and each of $R^2$ and $R^4$ is hydrogen. Also preferred are those compounds in which $R^3$ is a carbon-carbon bond, methylene, ethylene, trimethylene, tetramethylene, or 1,4-cyclohexylene. Thus preferred species include the (R,s) and (S,S) diastereomers of N-[3-(2-amino-4-hydroxy-5,6,7,8-tetrahydropyrido[2,3-d]pyrimidin-6-yl)-propioyl]-L-glutamic acid; N-[4-(2-amino-4-hydroxy-5,6,7,8-tetrahydropyrido[2,3-d]pyrimidin-6-yl)butyryl]-L-glutamic acid; N-[5-(2-amino-4-hydroxy-5,6,7,8-tetrahydropyrido[2,3-d]pyrimidin-6-yl)pentanoyl]-L-glutamic acid; N-[6-(2-amino-4-hydroxy-5,6,7,8-tetrahydropyrido[2,3-d]pyrimidin-6-yl)hexanoyl]-L-glutamic acid; N-[6(2-amino-4-hydroxy-5,6,7,8-tetrahydropyrido[2,3-d]-pyrimidin-6-yl)heptanoyl]-L-glutamic acid; and N-[4-(2{2-amino-4-hydroxy-5,6,7,8-tetrahydropyrido[2,3-d]-pyrimidin-6-yl}ethyl)cyclohex-1-ylcarbonyl]-L-glutamic acid.

The compounds of the present invention often can be employed advantageously in the form of a pharmaceutically acceptable salt. Such forms, including hydrates thereof, are often crystalline and advantageous for forming solutions or formulating pharmaceutical compositions. Pharmaceutically acceptable salts with bases include those formed from the alkali metals, alkaline earth metals, non-toxic metals, ammonium, and mono-, di- and trisubstituted amines, such as for example the sodium, potassium, lithium, calcium, magnesium, aluminum, zinc, ammonium, trimethylammonium, triethanolammonium, pyridinium, and substituted pyridinium salts. The mono and disodium salts, particularly the disodium salt, are advantageous.

The compounds of this invention in which $R^3$ is alkylene can be prepared through catalytic hydrogenation of a compound of the formula:

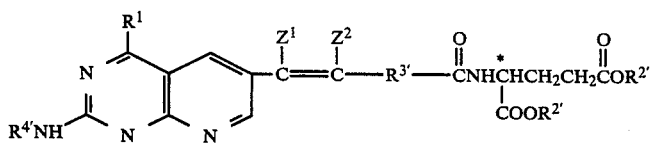

in which:
$Z^1$ and $Z^2$ taken individually are each hydrogen or taken together are a carbon-carbon bond;
$R^1$ is as herein defined;
$R^{2'}$ is a carboxy protecting group;
$R^{3'}$ is a carbon-carbon bond or alkylene of 1 to 4 carbon atoms; and
$R^{4'}$ is an amino protecting group.

Suitable hydrogenation catalysts include noble metals and noble metal oxides such as palladium or platinum oxide, rhodium oxide, and the foregoing on a support such as carbon or calcium oxide.

There is obtained a mixture of diastereomers of Formulas IA and IB in which $R^{2'}$ is a carboxy protecting group, and $R^{4'}$ is an amino protecting group. These protecting groups can then be removed through acidic or basic hydrolysis, as for example with sodium hydroxide, to yield the compounds of Formula I in which each of $R^2$ and $R^4$ is hydrogen.

Compounds of Formula II can be prepared utilizing procedures analogous to those described in European Patent Application No. 87308921.3. Thus a compound of the formula:

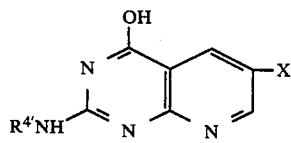

in which X is bromo or iodo and $R^{4'}$ is as herein defined, is allowed to react with an unsaturated compound of the formula:

in which $Z^1$, $Z^2$, $R^{2'}$, and $R^{3'}$ are as herein defined, in the presence of a palladium/trisubstituted phosphine catalyst of the type described by Sakamoto, *Synthesis*, 1983, 312 et seq.

There thus is obtained a compound of Formula II in which $R^1$ is —OH. When a compound of Formula I in which $R^1$ is —NH₂ is desired, this product can be treated with 1,2,4-triazole and (4-chlorophenyl)dichlorophosphate and the product of this reaction then treated with concentrated ammonia.

The compounds of this invention in which $R^3$ is cyclohexylene can be prepared through initial catalytic hydrogenation of a compound of the formula:

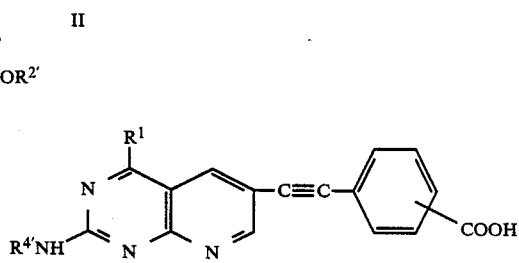

in which $R^{4'}$ is an amino protecting group and $R^1$ is a herein defined. Compounds of Formula V in which $R^1$ is —OH are prepared analogously to the methods described in European Pat. Application No. 87308921.3 and the corresponding compounds in which $R^1$ is —NH₂ are generated therefrom in the manner described above.

Suitable catalysts for the hydrogenation of compounds of Formula V include noble metals and noble metal oxides such as palladium or platinum oxide. Thus obtained is a compound of the formula:

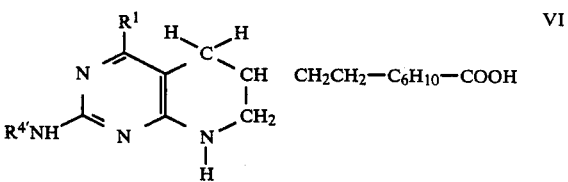

Compounds of Formula VI then are coupled with a protected glutamic acid derivative of the formula:

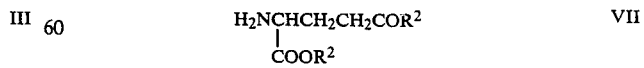

in which $R^{2'}$ is a carboxy protecting group, in the manner generally described in PCT application WO 86/05181, utilizing conventional condensation techniques for forming peptide bonds, such as activation of the carboxy group through formation of a mixed anhydride, treatment with DCC, or use of diphenylchlorophosphonate. Protecting groups designated by $R^{2'}$ and $R^{4'}$ then are removed in the manner described above.

The mixture of the individual diastereomers depicted by Formulas IA and IB can be used therapeutically as such or can be separated mechanically as by chromatography. Alternatively, the individual diastereomers can be separated by forming diastereomeric salts with a chiral acid such as the individual enantiomers of 10-camphorsulfonic acid, camphoric acid, alpha-bromocamphoric acid, methoxyacetic acid, tartaric acid, diacetyltartaric acid, malic acid, pyrrolidone-5-carboxylic acid, and the like, and then freeing one or both of the individual diastereomeric bases, optionally repeating the process, so as obtain either or both substantially free of the other; i.e., in a form having an optical purity of >95%. This separation can be effected before or after removal of any protecting groups.

As noted, the compounds of this invention have an effect on one or more enzymes which utilize folic acid, and in particular metabolic derivatives of folic acid, as a substrate. The compounds can be used, under the supervision of qualified professionals, to inhibit the growth of neoplasms including choriocarcinoma, leukemia, adenocarcinoma of the female breast, epidermid cancers of the head and neck, squamous or small-cell lung cancer, and various lymphosarcomas. The compounds can also be used to treat mycosis fungoides and psoriasis.

The compounds can be administered orally but preferably are administered parenterally, alone or in combination with other therapeutic agents including other anti-neoplastic agents, steroids, etc., to a mammal suffering from neoplasm and in need of treatment. Parenteral routes of administration include intramuscular, intrathecal, intravenous and intra-arterial. Dosage regimens must be titrated to the particular neoplasm, the condition of the patient, and the response but generally doses will be from about 10 to about 100 mg/day for 5-10 days or single daily administration of 250-500 mg, repeated periodically; e.g. every 14 days. While having a low toxicity as compared to other antimetabolites now in use, a toxic response often can be eliminated by either or both of reducing the daily dosage or administering the compound on alternative days or at longer intervals such as every three days. Oral dosage forms include tablets and capsules containing from 1-10 mg of drug per unit dosage. Isotonic saline solutions containing 20-100 mg/ml can be used for parenteral administration.

The following examples will serve to further illustrate the invention. In the NMR data, "s" denotes singlet, "d" denotes doublet, "t" denotes triplet, "q" denotes quartet, "m" denotes multiplet, and "br" denotes a broad peak.

EXAMPLE 1

Dimethyl N-[6-(2-pivaloylamino-4-hydroxypyrido[2,3-d]-pyrimidin-6-yl)hex-5-ynoyl]-L-glutamate A mixture of 1.94 g. (6 mmol.) of 2-pivaloyl amino-4-hydroxy-6-bromopyrido[2,3-d]pyrimidine, 1.6 g. (6 mmol.) of dimethyl N-(hex-5-ynoyl)-L-glutamate, 0.11 g. of palladium chloride, 0.32 g. of triphenylphosphine, 0.05 g. of cuprous iodide, and 2.6 mL. of triethylamine in 150 mL. of acetonitrile was heated at reflux for 3 hours and then cooled to ambient temperature. The solvent was removed under reduced pressure and the residue chromatographed on silica gel with 1:9 methanol: methylene chloride to yield dimethyl N-[6-(2-pivaloylamino-4-hydroxypyrido[2,3-d]pyrimidin-6-yl)hex-5-ynoyl]-L-glutamate, m.p. 159°-160° C. Anal. Calc. for $C_{25}H_{31}N_5O_7$: C, 58.47; H, 6.08; N, 13.64. Found: C, 58.23; H, 5.97; N, 13.43.

In as similar fashion by substituting an equivalent amount of dimethyl N-(pent-4-ynoyl)-L-glutamate for dimethyl N-(hex-5-ynoyl)-L-glutamate in the foregoing procedure, there can be obtained dimethyl N-[5-(2-pivaloylamino-4-hydroxypyrido[2,3-d]pyrimidin-6-yl)pent-4-ynoyl]-L-glutamate. In a representative experiment, the following physical constants were obtained for this compound: m.p. 162°-163° C. Anal. Calc. for $C_{24}H_{29}N_5O_7$: C, 57.71; H, 5.84; N, 14.02. Found: C, 57.94; H, 5.72; N, 13.99.

Likewise from dimethyl N-acryloyl-L-glutamate and dimethyl N-(but-3-ynoyl)-L-glutamate there are respectively obtained dimethyl N-[3-(2-pivaloylamino-4-hydroxypyrido[2,3-d]pyrimidin-6-yl)acryloyl]-L-glutamate and dimethyl N-[4-(2-pivaloylamino-4-hydroxypyrido[2,3-d]pyrimidin-6-yl)but-3-ynoyl]-L-glutamate.

By substituting an equivalent amount of dimethyl N-(hept-6-enoyl)-L-glutamate for dimethyl N-(hex-5-yn-oyl)-L-glutamate in the foregoing procedure, there can be obtained dimethyl N-[7-(2-pivaloylamino-4-hydroxypyrido[2,3-d]pyrimidin-6-yl)hept-6-enoyl]-L-glutamate. In a representative experiment, the following physical constants were obtained for this compound: m.p. 79°-81° C. Anal. Calc. for $C_{26}H_{35}N_5O_7$: C, 58.97; H, 6.66; N, 13.22. Found: C, 58.47; H, 6.48; N, 12.80.

Dimethyl N-(hex-5-ynoyl)-L-glutamate can be obtained by allowing hex-5-ynoic acid chloride (obtained by treating hex-5-ynoic acid with thionyl chloride) to react with dimethyl L-glutamate in the presence of an acid acceptor such as triethylamine. Hex-5-ynoic acid in turn can be prepared, for example, by alkaline hydrolysis of 5-cyanopent-1-yne.

Dimethyl N-acryloyl-L-glutamate, dimethyl N-(pent-4-ynoyl)-L-glutamate, dimethyl N-(but-3-ynoyl)-L-glutamate, and dimethyl N-(hept-6-enoyl)-L-glutamate are obtained similarly from the acid chlorides of acrylic acid, pent-4-ynoic acid, but-3-ynoic acid, and hept-6-enoic acid, respectively, and dimethyl L-glutamate.

EXAMPLE 2

Dimethyl N-[6-(2-Pivaloylamino-4-hydroxy-5,6,7,8-tetrahydropyrido[2,3-d]pyrimidin-6-yl)hexanoyl]-L-glutamate To a solution of 1.0g. of dimethyl N-[6-(2-pivaloylamino-4-hydroxypyrido[2,3-d]pyrimidin-6-yl)hex-5-ynoyl]-L-glutamate in 20mL. of glacial acetic acid were added 300 mg. of platinum oxide. The mixture was hydrogenated under one atmosphere pressure with agitation for 4 hours, the catalyst removed by filtration, and the filtrate concentrated under reduced pressure. Chromatography on silica gel eluting with 1:19 methanol:chloroform yielded 0.84 g. (82.7%) of dimethyl N-[6-(2-pivaloylamino-4-hydroxy-5,6,7,8-tetrahydropyrido[2,3-d]pyrimidin-6-yl)hexanoyl]-L-glutamate, m.p. 162°-166° C. Anal. Calc. for $C_{25}H_{39}N_5O_7$: C, 57.57; H, 7.54; N, 13.43. Found: C, 57.31; H, 7.25; N, 14.15.

Similarly prepared from dimethyl N-[5-(2-pivaloylamino-4-hydroxypyrido[2,3-d]pyrimidin-6-yl)pent-4-ynoyl]-L-glutamate is dimethyl N-[5-(2- pivaloylamino-4-hydroxy-5,6,7,8-tetrahydropyrido[2,3-d]pyrimidin-6yl)pentanoyl]-L-glutamate. In a representative experiment, the following physical constants were obtained for this compound: m.p. 151°–159° C.; Anal. Calc. for $C_{24}H_{37}N_5O_7$: C, 56.79; H, 7.35; N, 13.80. Found: C, 57.06; H, 7.22; N, 13.86.

Likewise dimethyl N-[3-(2-pivaloylamino-4-hydroxy-5,6,7,8-tetrahydropyrido[2,3-d]pyrimidin-6-yl)propionyl]-L-glutamate and dimethyl N-[4-(2-pivaloylamino-4-hydroxy-5,6,7,8-tetrahydropyrido[2,3-d]pyrimidin-6-yl)butyryl]-L-glutamate are prepared from N-[3-(2-pivaloylamino-4-hydroxypyrido[2,3-d]pyrimidin-6-yl)acryloyl]-L-glutamate and dimethyl N-[4-(2-pivaloylamino-4-hydroxypyrido[2,3-d]pyrimidin-6-yl)but-3-ynoyl]-L-glutamate, respectively.

By utilizing an equivalent amount of dimethyl N-[7-(2-pivaloylamino-4-hydroxypyrido[2,3-d]pyrimidin-6-yl)hept-6-enoyl]-L-glutamate, there is obtained dimethyl N-[7-(2-pivaloylamino-4-hydroxy-5,6,7,8-tetrahydropyrido[2,3-d]pyrimidin-6-yl)heptanoyl]-L-glutamate In a representative experiment, the following physical constants were obtained for this compound: m.p. 152°–160° C. Anal. Calc. for $C_{26}H_{41}N_5O_7$:C, 58.30; H, 7.72; N, 13.08. Found: C, 58.51; H, 7.61; N, 12.87.

EXAMPLE 3

Diethyl N-[4-{2-(2-Pivaloylamino-4-hydroxy-5,6,7,8-tetrahydropyrido[2,3-d]pyrimidin-6-yl)ethyl}cyclohex-1-yl]-L-glutamate A. Five grams of 2-pivaloylamino-4-hydroxy-6-(4-carboxyphenylethynyl)pyrido[2,3-d]pyrimidine described in European Pat. Application No. 87308921.3) and 1.60 g. of platinum oxide in 200mL. of trifluoroacetic acid were hydrogenated in a Parr apparatus at ambient temperature and 60 psi for 24 hours. Removal of the catalyst by filtration and concentration of the filtrate yielded 2-pivaloylamino-4-hydroxy-6-[2-(4-carboxycyclohex-1-yl)ethyl]-5,6,7,8-tetrahydropyrido[2,3-d]pyrimidine as a white solid which was further purified by column chromatography (Waters 200) eluting with 1:9 methanol:dichloromethane. m.p. 218°–234° C. Anal. Calc. for $C_{21}H_{32}N_4O_4$: C, 63.35; H, 7.97; N, 13.85. Found: C, 63.30; H, 7.48; N, 13.57.

B. To a solution of 2.40 g. of 2-pivaloylamino-4-hydroxy-6-[2-(4-carboxycyclohex-1-yl)ethyl]-5,6,7,8-tetrahydropyrido[2,3-d]pyrimidine in 50mL. of dry N-methylpyrrolidone and 2.25mL. of N-methylmorpholine were added 2.75 g. of phenyl N-phenylphosphoaminochloridate. This mixture was stirred at 0° C. under nitrogen for 45 minutes and 2.45g. of diethyl L-glutamate were then added and stirring at ambient temperatures then was continued for 72 hours. The solvent was removed by distillation at 0.2 mm/60° C. and the residue chromatographed on silica gel, eluting with 1:19 methanol:chloroform to yield 1.67 g. (48%) of diethyl N-[4-{2-(2-pivaloylamino-4-hydroxy-5,6,7,8-tetrahydropyrido[2,3-d]pyrimidin-6-yl)ethyl}cyclohex-1-yl]-L-glutamate, m.p. 160°–170° C. Anal. Calc. for $C_{30}H_{47}N_5O_7$: C, 61.10; H, 8.03; N, 11.87. Found: C, 61.38; H, 7.90; N, 11.84.

EXAMPLE 4

N-[6-(2-Amino-4-hydroxy-5,6,7,8-tetrahydropyrido[2,3-d]pyrimidin-6-yl)hexanoyl]-L-qlutamic Acid A solution of 0.5 g. of dimethyl N-[6-(2-pivaloylamino-4-hydroxy-5,6,7,8-tetrahydropyrido[2,3-d] -pyrimidin-6-yl)hexanoyl]-L-glutamate in 75 mL. of 1.0 N aqueous sodium hydroxide is stirred at room temperature for 120 hours and the pH then adjusted to 7.0 through the careful addition of 5.0 N hydrochloric acid. Water was removed under reduced pressure and the concentrated solution then cooled in an ice-bath. The solid which formed was collected by filtration and dried at 80° C. to yield N-[6-(2-amino-4-hydroxy-5,6,7,8-tetrahydropyrido-[2,3-d]pyrimidin-6-yl)hexanoyl]-L-glutamic acid, m.p. foaming at 135° C., melting at 180°–195° C. NMR (DMSO-$d_6$ 300 MHz) delta: 9.80 (s, br, 1H), 7.90 (s, J=8 Hz, 1H), 6.20 (s, 1H), 5.95 (s, 2H), 4.08 (m, 1H), 3.10 (m, 1H), 2.63 (t, J=10 Hz, 1H), 2.40 (m, 1H), 2.20 (t, J=8 Hz, 2H), 2.05 (t, J=8 Hz, 2H), 1.84 (m, 1H), 1.70 (m, 2H), 1.55 (m, 3H), 1.20 (m, 6H).

Similarly prepared from dimethyl N-[5-(2-pivaloylamino-4-hydroxy-5,6,7,8-tetrahydropyrido[2,3-d]-pyrimidin-6-yl)pentanoyl]-L-glutamate is N-[5-(2-amino-4-hydroxy-5,6,7,8-tetrahydropyrido[2,3-d]pyrimidin-6yl)pentanoyl]-L-glutamic acid. In a representative experiment, the following physical constants were obtained for this compound: m.p. 144° C. (softening and foaming); NMR (DMSO-$d_6$ 300 MHz) delta: 9.70 (s, br, 1H), 8.01 (d, J=6 Hz, 1H), 6.17 (s, 1H), 5.88 (s, 2H), 4.13 (m, 1H), 3.17 (m, 1H), 2.68 (t, J=6 Hz, 1H), 2.42 (m, 1H), 2.22 (t, J=5 Hz, 2H), 2.07 (t, J=5 Hz, 2H), 1.88 (m, 1H), 1.70 (m, 2H), 1.44 (m, 3H), 1.24 (m, 4H);

N-[3-(2-Amino-4-hydroxy-5,6,7,8-tetrahydropyrido-[2,3-d]pyrimidin-6-yl)propionyl]-L-glutamic acid and N-[4-(2-amino-4-hydroxy-5,6,7,8-tetrahydropyrido[2,3-d]-pyrimidin-6-yl)butyryl]-L-glutamic acid are prepared analogously from dimethyl N-[3-(2-pivaloylamino-4-hydroxy-5,6,7,8-tetrahydropyrido[2,3-d]pyrimidin-6yl)propionyl]-L-glutamate and dimethyl N-[4-(2-pivaloylamino-4-hydroxy-5,6,7,8-tetrahydropyrido[2,3d]pyrimidin-6-yl)butyryl]-L-glutamate, respectively.

In a similar fashion, N-[7-(2-amino-4-hydroxy-5,6,7,8-tetrahydropyrido[2,3-d]pyrimidin-6-yl)heptanoyl-]-L-glutamic acid is prepared from dimethyl N-[7-(2-pivaloylamino-4-hydroxy-5,6,7,8-tetrahydropyrido-[2,3-d]pyrimidin-6-yl)heptanoyl]-L-glutamate. In a representative experiment, the following physical constants were obtained for this compound: m.p. 185°–195° C. (foaming); NMR (DMSO-$d_6$ 300 MHz) delta: 9.68 (s, br, 1H), 8.01 (d, J=10 Hz, 1H), 6.20 (s, 1H), 5.88 (s, 2H), 4.14 (m, 1H), 3.10 (m, 1H), 2.66 (t, J=9 Hz, 1H), 2.35 (m, 1H), 2.20 (t, J=5 Hz, 2H), 2.05 (t, J=5 Hz, 2H), 1.89 (m, 1H), 1.67 (m, 2H), 1.45 (m, 3H), 1.20 (m, 8H).

Analogously by employing diethyl N-[4-{2-(2-pivaloylamino-4-hydroxy-5,6,7,8-tetrahydropyrido[2,3-d]-pyrimidin-6-yl)ethyl}cyclohex-1-yl]-L-glutamate, there is obtained N-[4-{2-(2-amino-4-hydroxy-5,6,7,8-tetrahydropyrido[2,3-d]pyrimidin-6-yl)ethyl}cyclohex-1-yl]-L-glutamic acid. In a representative experiment, the following physical constants were obtained for this compound: m.p. 210°–225° C. NMR (DMSO-$d_6$ 300 MHz) delta: 9.70 (s, br, 1H), 7.90 (m, 1H), 6.23 (s, 1H), 5.92 (s, 2H), 4.17 (m, 1H), 3.18 (m, 1H), 2.72 (t, J=9 Hz, 1H), 2.45 (m, 1H), 2.27 (t, J=6 Hz, 2H), 2.09 (m, 1H), 1.96 (m, 1H), 1.74 (m, 3H), 1.45 (m, 5H), 1.27 (m, 8H).

EXAMPLE 5

The $IC_{50}$ in whole cell human leukemia cell lines, CCRF-CEM, of representative compounds of this invention are as follows:

| R¹ | R² | R³ | R⁴ | ug/mL |
|---|---|---|---|---|
| OH | H | —(CH₂)₂— | H | 0.023 |
| OH | H | —(CH₂)₃— | H | 0.0075 |
| OH | H | —(CH₂)₄— | H | 0.034 |
| OH | H | 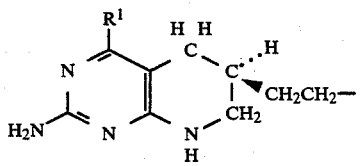 | H | 0.007 |

What is claimed is:

1. A compound selected from the group consisting of a glutamic acid derivative having the formula:

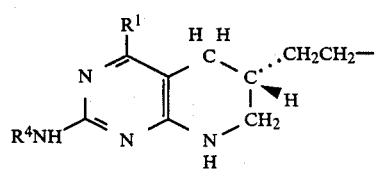

in which:
R¹ is —OH or —NH₂;
R³ is a carbon-carbon bond, alkylene of 1 to 4 carbon atoms, or cyclohexylene;
the configuration about the carbon atom designated * is S; and
the pharmaceutically acceptable salts thereof.

2. A compound according to claim 1 wherein R¹ is —OH.

3. A compound according to claim 2 wherein R³ is a carbon-carbon bond, methylene, ethylene, trimethylene, or tetramethylene.

4. A compound according to claim 3 which is (S,S)-N-[3-(2-amino-4-hydroxy-5,6,7,8-tetrahydropyrido[2,3-d]-pyrimidin-6-yl)propioyl]-L-glutamic acid or (R,S)-N-[3-(2-amino-4-hydroxy-5,6,7,8-tetrahydropyrido-[2,3-d]pyrimidin-6-yl)propioyl]-L-glutamic acid.

5. A compound according to claim 3 which is (S,S)-N-[4-(2-amino-4-hydroxy-5,6,7,8-tetrahydropyrido[2,3-d]-pyrimidin-6-yl)butyryl]-L-glutamic acid or (R,S)-N-[4-(2-amino-4-hydroxy-5,6,7,8-tetrahydropyrido-[2,3-d]pyrimidin-6-yl)butyryl]-L-glutamic acid.

6. A compound according to claim 3 which is (S,S)-N-[5-(2-amino-4-hydroxy-5,6,7,8-tetrahydropyrido[2,3-d]-pyrimidin-6-yl)pentanoyl]-L-glutamic acid or (R,S)-N-[5-(2-amino-5-hydroxy-5,6,7,8-tetrahydropyrido-[2,3-d]pyrimidin-6-yl)pentanoyl]-L-glutamic acid.

7. A compound according to claim 3 which is (S,S)-N-[6(2-amino-4-hydroxy-5,6,7,8-tetrahydropyrido[2,3-d]-pyrimidin-6-yl)hexanoyl]-L-glutamic acid or (R,S)-N[6-(2-amino-6-hydroxy-5,6,7,8-tetrahydropyrido-[2,3-d]pyrimidin-6-yl)hexanoyl]-L-glutamic acid.

8. A compound according to claim 3 which is (S,S)-N-[7(2-amino-4-hydroxy-5,6,7,8-tetrahydropyrido[2,3-d]-pyrimidin-6-yl)heptanoyl]-L-glutamic acid or (R,S)-N-[7-(2-amino-6-hydroxy-5,6,7,8-tetrahydropyrido-[2,3-d]pyrimidin-6-yl)heptanoyl]-L-glutamic acid.

9. A compound according to claim 2 wherein R³ is 1,4-cyclohexylene.

10. The method of inhibiting neoplastic growth in a mammal which growth is dependent on folic acid or a metabolic derivative of folic acid as a substrate, which comprises administering to the mammal in a single or multiple dose regimen an effective amount of a compound according to claim 1.

11. A pharmaceutical composition for inhibiting neoplastic growth in a mammal which growth is dependent on folic acid or a metabolic derivative of folic acid as a substrate, which comprises an amount of a compound according to claim 1 which upon administration to the mammal in a single or multiple dose regimen is effective to inhibit said growth, in combination with a pharmaceutically acceptable carrier.

12. A pharmaceutical composition for combatting neoplastic growth in a mammal which comprises an amount of a compound according to claim 1 which upon administration to the mammal in a single or multiple dose regimen is effective to combat said growth, in combination with a pharmaceutically acceptable carrier.

13. A compound selected from the group consisting of a glutamic acid derivative having the formula:

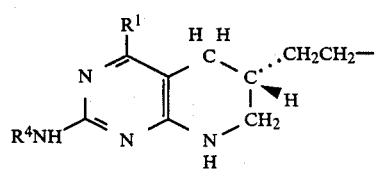

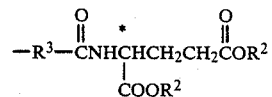

or

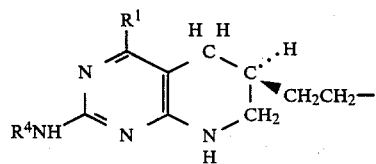

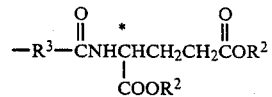

in which:
R¹ is —OH or —NH₂;
R² is hydrogen or a carboxy protecting group selected from the group consisting of (a) a straight or branched lower alkyl ester which is unsubstituted or substituted in the 1- or 2-position with (i) lower alkoxy, (ii) lower alkylthio, (iii) halogen, (iv) phenyl which is unsubstituted or mono-, di- or tri-substituted with lower alkyl, lower alkoxy, hydroxy, halo, or nitro, or (v) aroyl, or (b) a silyl group;
R³ is a carbon-carbon bond, alkylene of 1 to 4 carbon atoms, or cyclohexylene;
R⁴ is hydrogen or an unsubstituted or substituted acyl amino protecting group;
at least one of R² and R⁴ being other than hydrogen; and
the configuration about the carbon atom designated * is S[; and the pharmaceutically acceptable salts thereof.

* * * * *

UNITED STATES PATENT AND TRADEMARK OFFICE
CERTIFICATE OF CORRECTION

PATENT NO. : 4,882,333
DATED : November 21, 1989
INVENTOR(S) : Chuan Shih et al.

It is certified that error appears in the above-identified patent and that said Letters Patent is hereby corrected as shown below:

Column 9, lines 13-34, and col. 10, lines 20-27:

Claims 1 and 13 should read as follows:

1. A compound selected from the group consisting of a glutamic acid derivative having the formula:

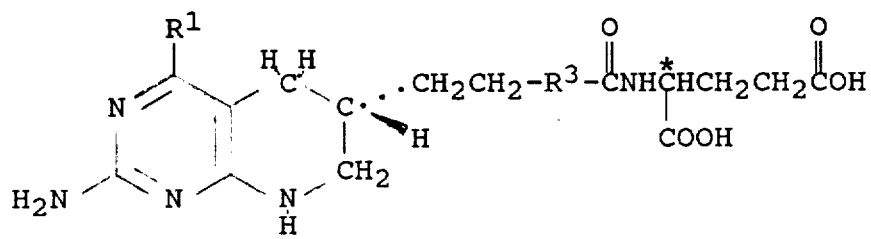

or

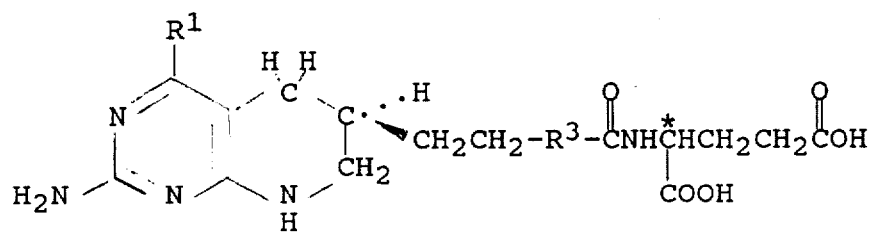

in which:

$R^1$ is -OH or $-NH_2$;

UNITED STATES PATENT AND TRADEMARK OFFICE
CERTIFICATE OF CORRECTION

PATENT NO. : 4,882,333
DATED : November 21, 1989
INVENTOR(S) : Chuan Shih et al.

It is certified that error appears in the above-identified patent and that said Letters Patent is hereby corrected as shown below:

$R^3$ is a carbon-carbon bond, alkylene of 1 to 4 carbon atoms, or cyclohexylene;

the configuration about the carbon atom designated * is S; and the pharmaceutically acceptable salts thereof. --

13. A compound selected from the group consisting of a glutamic acid derivative having the formula:

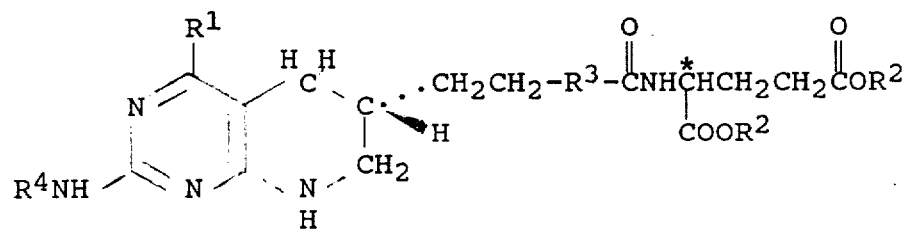

or

UNITED STATES PATENT AND TRADEMARK OFFICE
CERTIFICATE OF CORRECTION

PATENT NO. : 4,882,333
DATED : November 21, 1989
INVENTOR(S) : Chuan Shih et al.

It is certified that error appears in the above-identified patent and that said Letters Patent is hereby corrected as shown below:

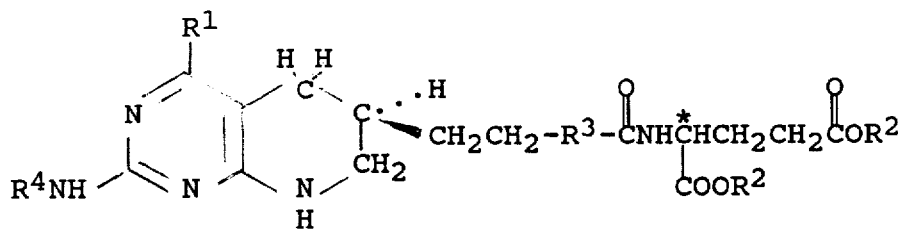

in which:

$R^1$ is -OH or -$NH_2$;

$R^2$ is hydrogen or a carboxy protecting group selected from the group consisting of (a) a straight or branched lower alkyl ester which is unsubstituted or substituted in the 1- or 2-position with (i) lower alkoxy, (ii) lower alkylthio, (iii) halogen, (iv) phenyl which is unsubstituted or mono-, di- or tri-substituted with lower alkyl, lower alkoxy, hydroxy, halo, or nitro, or (v) aroyl, or (b) a silyl group;

UNITED STATES PATENT AND TRADEMARK OFFICE
CERTIFICATE OF CORRECTION

PATENT NO. : 4,882,333

DATED : November 21, 1989

INVENTOR(S) : Chuan Shih et al.

It is certified that error appears in the above-identified patent and that said Letters Patent is hereby corrected as shown below:

$R^3$ is a carbon-carbon bond, alkylene of 1 to 4 carbon atoms, or cyclohexylene;

$R^4$ is hydrogen or an unsubstituted or substituted acyl amino protecting group;

at least one of $R^2$ and $R^4$ being other than hydrogen; and the configuration about the carbon atom designated * is S.

Signed and Sealed this

Twenty-fourth Day of December, 1991

Attest:

HARRY F. MANBECK, JR.

Attesting Officer  Commissioner of Patents and Trademarks